(12) United States Patent
Shepherd et al.

(10) Patent No.: US 7,873,198 B2
(45) Date of Patent: Jan. 18, 2011

(54) METHODS AND APPARATUS FOR DETERMINING PROPORTIONS OF BODY MATERIALS

(75) Inventors: John A. Shepherd, Fairfax, CA (US); Serghei Malkov, Mountain View, CA (US); Steven R. Cummings, Mill Valley, CA (US)

(73) Assignees: Sutter West Bay Hospitals, San Francisco, CA (US); The Regents of the University of California, Oakland, CA (US)

( * ) Notice: Subject to any disclaimer, the term of this patent is extended or adjusted under 35 U.S.C. 154(b) by 274 days.

(21) Appl. No.: 11/922,289

(22) PCT Filed: Jun. 15, 2006

(86) PCT No.: PCT/US2006/023811

§ 371 (c)(1),
(2), (4) Date: Nov. 14, 2008

(87) PCT Pub. No.: WO2006/138717

PCT Pub. Date: Dec. 28, 2006

(65) Prior Publication Data

US 2009/0076382 A1    Mar. 19, 2009

Related U.S. Application Data

(60) Provisional application No. 60/691,745, filed on Jun. 16, 2005, provisional application No. 60/779,792, filed on Mar. 6, 2006.

(51) Int. Cl.
*G06K 9/00* (2006.01)
*G06K 9/68* (2006.01)

(52) U.S. Cl. .................................. 382/132; 382/218
(58) Field of Classification Search ................. 382/128, 382/132, 190, 218; 378/53, 56, 207

See application file for complete search history.

(56) References Cited

U.S. PATENT DOCUMENTS

| 5,657,362 | A  | 8/1997  | Giger et al.     |
| 5,768,334 | A  | 6/1998  | Maitrejean et al.|
| 5,844,965 | A  | 12/1998 | Galkin et al.    |
| 6,516,045 | B2 | 2/2003  | Shepherd et al.  |
| 6,674,835 | B2 | 1/2004  | Kaufhold et al.  |

*Primary Examiner*—Daniel G Mariam
(74) *Attorney, Agent, or Firm*—Joseph R. Baker, Jr.; Gavrilovich Dodd & Lindsey LLP

(57) ABSTRACT

The present invention provides an apparatus and methods for measuring proportions of body materials in body parts. The apparatus includes a device for retaining the body part, at least one reference material with at least two thicknesses positioned adjacent to the device, and at least three radiopaque markers positioned on the reference material(s). The reference material(s) each have an attenuation characteristic that is selected in correspondence to the body materials in the body part. The apparatus further includes a radiation device to simultaneously irradiate the body part, the reference material (s) and the radiopaque markers as well as a detector to detect attenuated beams of radiation and a pattern projected from the irradiated radiopaque markers. A calculation device determines the thickness of the body part based on this projected pattern and compares the attenuation values of the body part and the reference material(s) at the determined thickness.

48 Claims, 3 Drawing Sheets

METHODS AND APPARATUS FOR DETERMINING PROPORTIONS OF BODY MATERIALS

CROSS-REFERENCE TO RELATED APPLICATIONS

This application is a National Stage Application filed under 35 U.S.C. §371, which is based upon and claims priority to International Application No. PCT/US2006/023811, filed Jun. 15, 2006, which application claims priority under 35 U.S.C. §119 to U.S. Provisional Application Ser. No. 60/691,745 filed Jun. 16, 2005, and to U.S. Provisional Application Ser. No. 60/779,792 filed Mar. 6, 2006, the disclosures of which are incorporated herein by reference.

FIELD OF THE INVENTION

The present invention relates generally to radiography. More particularly, the present invention relates to methods and an apparatus for measuring proportions of body materials in body parts of humans and animals.

BACKGROUND

The determination of proportions or densities of different body materials in body parts of humans or animals is of utmost importance to monitor, for instance, cancer risk in clinical drug trials, epidemiological studies, or routine screening. The measures of proportions or densities could be shown to be useful as markers to predict, for instance, breast cancer risk and possibly risk of disease recurrence or change in breast cancer risk.

To obtain these measures, techniques have been developed to maximize the radiographic contrast of tissue composition of a body part to better discriminate cancer risk. The X-ray energies, dose levels, and film/screen combinations are typically designed to maximize the radiographic tissue composition contrast. As an example, breast density was initially described using a semi-quantitative classification system that took into account the quantitative (amount of density) and qualitative nature of the density (diffuse or associated with ductal structures). Four to ten category systems have been previously used to cover the entire density range. A more quantitative approach measures the area of mammographically dense breast area relative to the total projected breast area, referred to as mammographic density. Mammographic density is a quantitative continuous grading from 0 to 100% density measured by delineating the radiographically dense areas in the mammogram from the entire breast area and providing a percentage breast density. Although mammographic density is currently a widely used technique, it has serious limitations. First, since the films are uncalibrated for mass density versus film optical density, a unique threshold has to be picked for each film. Second, the total and dense projected areas will change based on the amount of compression. For example, in a typical laboratory, the reproducibility of delineating the dense regions by an expert radiologist on the same image is approximately 5-7%. If both delineation errors and patient repositioning errors are conservatively assumed to be 7%, the 95% confidence for a significant change in density is approximately 14%. Thus, the sensitivity for risk classification and change in follow-up examinations is similar to that of the categorical methods.

Accurate measurement of compressed breast thickness is an important factor in determining breast density. However, the measurement of actual thickness provided by commercial mammography systems can be as much as one centimeter off the actual thickness due to deflection of the breast compression plate.

Accordingly there is a need in the art to develop a device and method to quantify proportions or densities of different body materials in body parts of humans and animals that can more accurately determine the thickness of the body part under investigation.

SUMMARY OF THE INVENTION

The present invention provides an apparatus for determining a proportion of body materials in a body part. The apparatus includes a device for retaining the body part, and at least one reference material with at least two thicknesses positioned adjacent to the retaining device. Each reference material has an attenuation characteristic that is selected in correspondence to the body materials in the body part. At least three radiopaque markers are positioned on the reference material(s). The apparatus further includes a radiation device positioned to simultaneously irradiate the body part, the reference material(s) and the radiopaque markers. A detector is included in the apparatus to detect beams of radiation that are attenuated by the reference material(s) and the body part as attenuation values. The detector also detects a pattern projected from the irradiated radiopaque markers. The apparatus further contains a calculation device, which determines the thickness of the body part from the projected pattern of radiopaque markers. The calculation device also calculates the proportion of body materials that define the body part based on comparing the attenuation values of the body part to the attenuation values of the reference material(s) at the determined thickness.

The present invention also provides a method of determining a proportion of body materials in a body part. With this method, a device for retaining the body part as well as at least one reference material with at least two thicknesses are provided. Each reference material has an attenuation characteristic that is selected in correspondence to the body materials in the body part. Next, the reference material(s) are positioned adjacent to the retaining device and at least three radiopaque markers are positioned on the reference material(s). The body part, the reference material(s) and the radiopaque markers are then simultaneously irradiated, thereby creating beams that are attenuated by the reference material(s) and the body part and a pattern that is projected from the radiopaque markers. This pattern is used to determine the thickness of the body part. The attenuated beams are then detected by a detector as attenuation values. The attenuation value(s) of the reference material(s) at the determined body part thickness are then determined. In a final step, the proportion of body materials in the body part is calculated by comparing the attenuation values of the body part to the attenuation value(s) of the reference material(s) at the determined body part thickness.

The present invention also provides a method of creating a regression model for determining a proportion of body materials in a body part. With this method, a device for retaining a body part is provided. Next, either at least one reference material with at least two thicknesses, or at least two reference materials are provided and positioned adjacent to the retaining device. The reference material(s) each have an attenuation characteristic that is selected in correspondence to the body materials in the body part. At this point, at least three radiopaque markers may be positioned on the reference material(s). Next, the body part, reference material(s) and optional radiopaque markers are irradiated, thereby creating beams that are attenuated by the reference material(s) and the body part. A pattern projected from the optional radiopaque markers would also be present if those were used. The attenuated beams are detected by a detector as attenuation values. If radiopaque markers were used, the projected pattern would then be used to determine the thickness of the body part and the attenuation values of the reference material(s) at that thickness. Next, data are collected relating to the irradiating, positioning, detecting and determining. The attenuation values of the reference material(s) are then validated and a regression model is created based on the collected data. This regression model is then used to predict attenuation values for the reference material(s) under different conditions.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
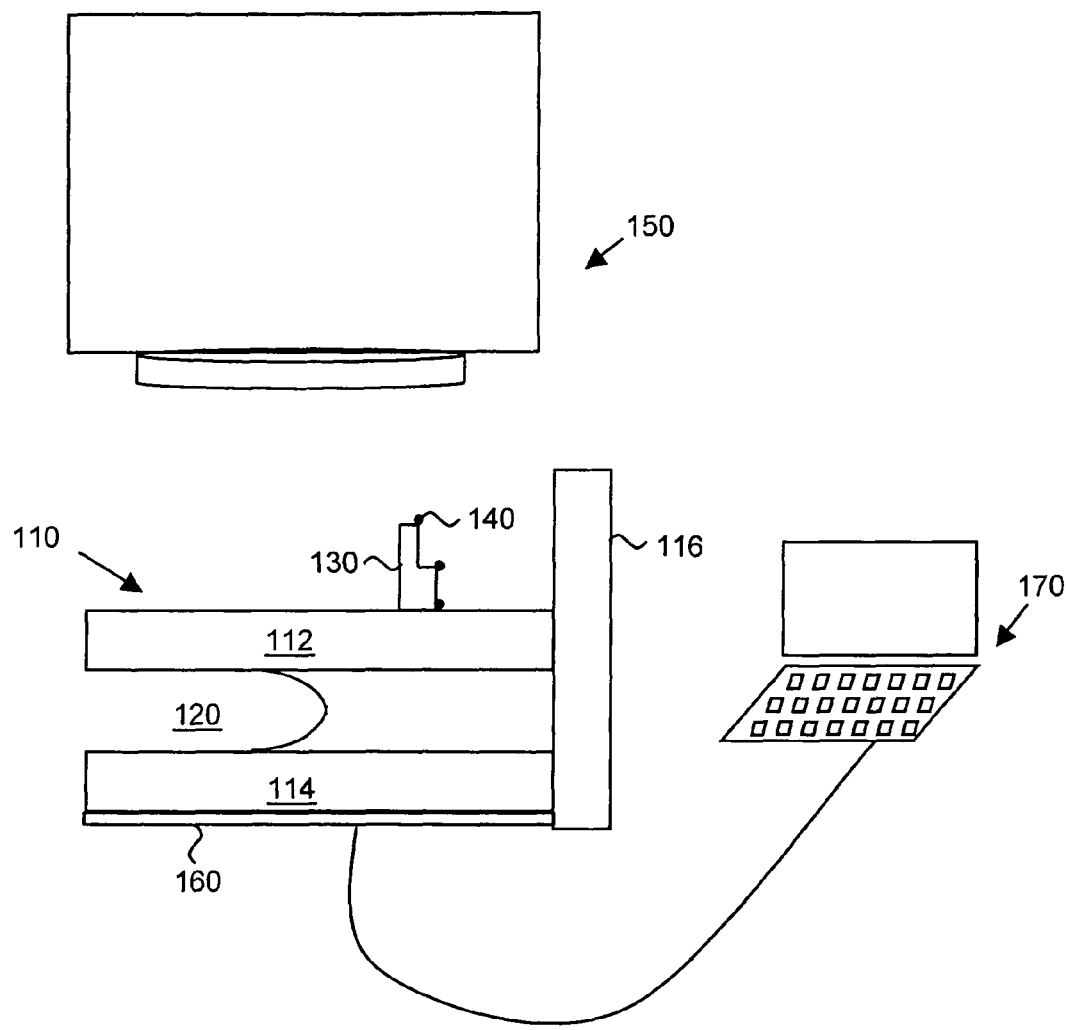
FIG. 1 shows an apparatus for determining a proportion of body materials in a body part according to the present invention.

The present invention provides an apparatus for determining a proportion of body materials in a body part. FIG. 1 shows an example of an apparatus according to the present invention. The apparatus contains a device 110 for retaining a body part 120 and at least one reference material 130 having at least two thicknesses. For purposes of illustration, one reference material with two thicknesses is shown in FIG. 1. Reference material 130 may, but need not, be positioned on top of device 110, as shown. Reference material 130 has an attenuation characteristic that is selected in correspondence to the body materials in body part 120. The reference material further has at least three radiopaque markers 140, preferably at least five radiopaque markers 140, three of which are shown in the figure. Radiopaque markers 140 may be any radiopaque material, including but not limited to metallic spheres. The apparatus also contains a radiation device 150, which is positioned to simultaneously irradiate body part 120, reference material 130 and radiopaque markers 140. The radiation device may be, for example, a single X-ray absorptiometer, a single photon absorptiometer, a mammography system, or a planar medical X-ray system. Radiation generated by radiation device 150 is attenuated by body part 120 and reference material 130 according to the attenuation characteristics of body part 120 and reference material 130. The attenuated radiation beams are detected by a detector 160 as attenuation values. Detector 160 also detects a pattern projected by radiopaque markers 140. Detector 160 may be, for example, film or a digital detector. The apparatus further contains a calculation device 170, which is used to determine the thickness of body part 120 from the projected pattern of radiopaque markers 140, and to calculate the proportion of body materials defining body part 120 based on comparing the attenuation of reference material 130 at the determined thickness to the attenuation of body part 120. The calculation device may be a desktop computer, workstation, laptop computer, etc. If detector 160 is a digital detector, it may be connected to calculation device 170, for example through cable 180 as shown or through a wireless connection. If detector 160 is film, the film is preferably scanned and digitized and the digitized image is then processed by calculation device 170.

Any body part may be analyzed according to the present invention. Examples of body parts include, but are not limited to, breast, muscle, organ, bone, and processed tissue. Examples of proportions of body materials that may be determined include, but are not limited to, breast density, muscle density, organ density, bone density, and processed tissue density.

Any reference material with attenuation characteristics in correspondence to the body materials of the body part may be selected. Preferably, the reference material has an attenuation characteristic equivalent to a fat or glandular tissue.

In another embodiment, at least two reference materials are used. In this embodiment, one of the reference materials preferably has an attenuation characteristic equivalent to a fat tissue, and another reference material preferably has an attenuation characteristic equivalent to a glandular tissue. In either embodiment, the reference material(s) are preferably attached to the retaining device to prevent movement of the reference material(s) on the retaining device. Also preferably, the reference material(s) and the at least three radiopaque markers are positioned such that the beams that are attenuated by the reference material(s) and the projected pattern of the radiopaque markers do not interfere with the beams that are attenuated by the body part.

Any retaining device may be used according to the present invention. Preferably, retaining device 110 includes, as shown in FIG. 1, a top radiolucent paddle 112 and a bottom translucent paddle 114, where body part 120 is retained between the two paddles. Also preferably, retaining device 110 includes a device 116 for adjusting retaining device 110 to retain body parts of different thicknesses.

The present invention also provides a method of determining a proportion of body materials in a body part using the above apparatus. Any body part may be analyzed according to the present invention, including but not limited to breast, organ, bone, muscle and processed tissue. The proportion of body materials in the body part may be, for example, breast density, organ density, bone density, muscle density, or processed tissue density.

In a first step of the method, a device for retaining a body part and at least one reference material having at least two thicknesses are provided. Each reference material is selected to have an attenuation characteristic that corresponds to the body materials in the body part. For example, in the case of a mammogram, the at least one reference material would emulate breast tissue. Thus, the at least one reference material preferably has an attenuation characteristic that corresponds to a fat or glandular tissue. Alternatively, at least two reference materials, having at least two thicknesses each, may be used. In this case, one reference material preferably has an attenuation characteristic that corresponds to a fat tissue, and another reference material preferably has an attenuation characteristic that corresponds to a glandular tissue.

Figure 2:
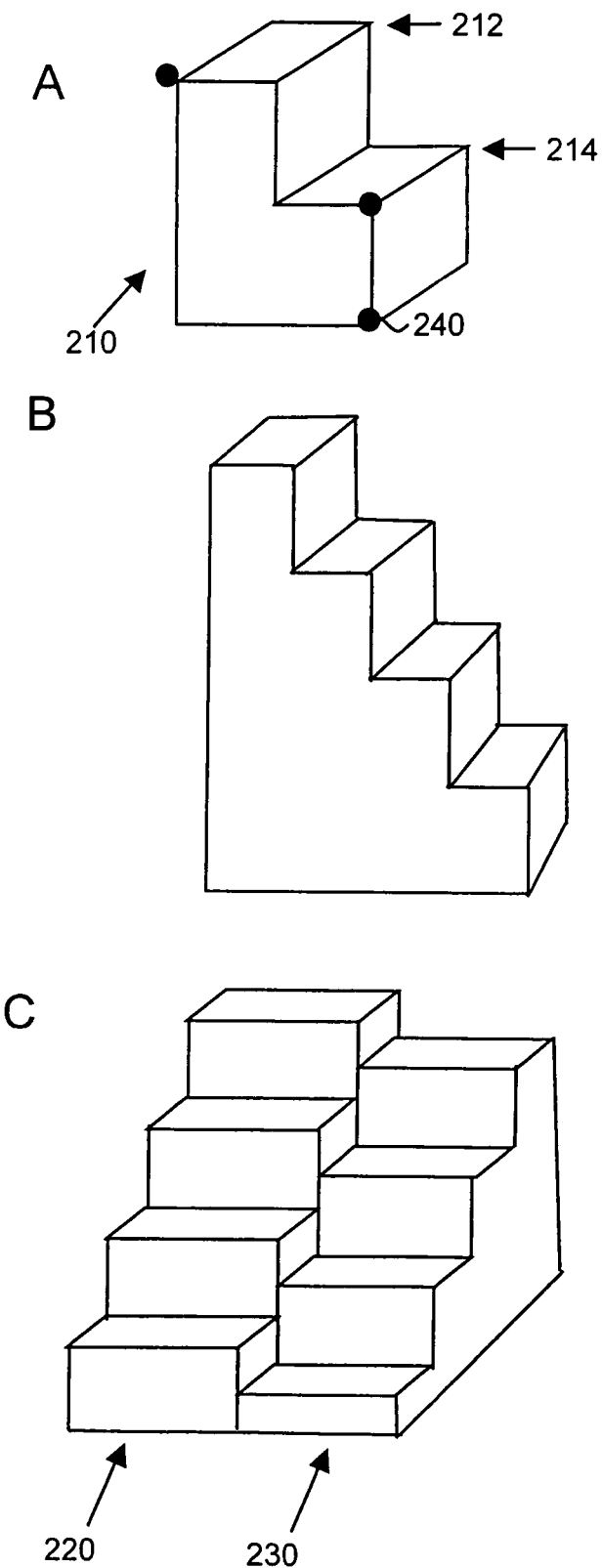
FIG. 2 shows examples of reference material configurations according to the present invention.

At least two thicknesses of the reference material are used that correspond to a range of body part thicknesses. FIG. 2A shows one reference material 210 with two heights 212 and 214 used to create two thicknesses. Preferably, a stepwise range of heights, as shown in FIG. 2B, is used to create different thicknesses. The step heights could be, for example, 1 cm, 3 cm, 5 cm, and 7 cm. If two reference materials are used, two sets of steps may be used. FIG. 2C shows one set of steps 220, made of one reference material, and a second set of steps 230 made of a different reference material. In this case, one set of steps could be made of a reference material with an attenuation characteristic that corresponds to a fat tissue, and the other set of steps could be made of a reference material with an attenuation characteristic that corresponds to a glandular tissue. Preferably, the steps of the two reference materials would be staggered as shown. For example, steps 220 could be 2, 4, 6, and 8 cm tall and steps 230 could be 1, 3, 5, and 7 cm tall.

The reference material preferably has at least three radiopaque markers 240. More preferably, the reference material has at least five radiopaque markers positioned on it to improve accuracy in determining the location of the reference material. The markers could be something similar to metallic spheres and are preferably automatically detected by an algorithm that defines them to be specific markers. Detection algorithms are known in the art and will not be described here. The reference material(s) with radiopaque markers may be referred to as a phantom, with phantoms having a stepwise configuration of reference material(s) referred to as a step phantom.

Next, the reference material(s) are positioned adjacent to the retaining device. In a preferred embodiment, the retaining device can be adjusted to retain body parts of different thicknesses. In a particularly preferred embodiment, the retaining device contains two radiolucent paddles, such that the body part is positioned between the two paddles and the reference material(s) are positioned on top of the top paddle. In this way, the reference material(s) will move up or down as the subject's body part is retained by the retaining device. Preferably, the positioning step includes the step of attaching the reference material(s) to the retaining device such that they are immobilized on the device. The reference material(s) may be attached to the retaining device with any suitable means, e.g. glue or other adhesive. By positioning the reference materials and radiopaque markers in a fixed position, the multiple radiopaque markers, as well as the imaging system, will have a predefined geometry that is known before imaging with a patient and that creates a unique projected pattern on the detector. The geometry of the radiopaque markers is defined as a set of vectors from a defined origin on the retaining device. Preferably, the vectors define the position of the radiopaque markers in the x, y, and z planes as well as 3 degrees of rotation.

Figure 3:
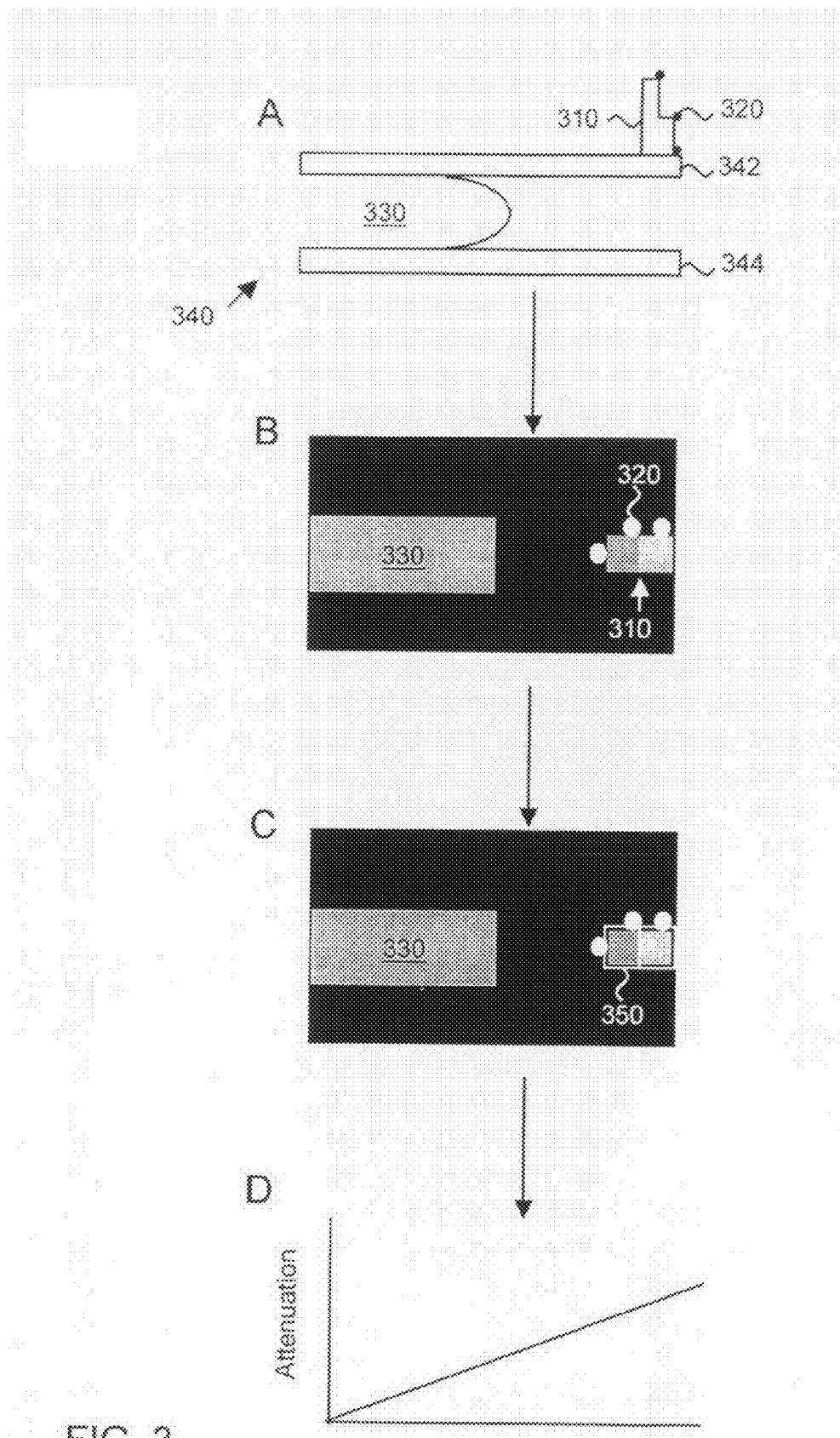
FIG. 3 shows a method of determining a proportion of body materials in a body part according to the present invention.

In the next step, shown in FIG. 3A, the at least one reference material 310, at least three radiopaque markers 320 and body part 330 are simultaneously irradiated. The irradiation creates beams that are attenuated by body part 330 and reference material(s) 310 and that are detected by a detector as attenuation values. In addition, the irradiation creates a projected pattern of the radiopaque markers on the detector. Preferably, reference material(s) 310 with radiopaque markers 320 are positioned such that the beams that are attenuated by reference material(s) 310 and the projected pattern of radiopaque markers 320 do not interfere with the beams that are attenuated by body part 330.

The projected pattern of radiopaque markers 320, and the attenuation values of body part 330 and at least one reference material 310 are used to create an image (FIG. 3B). This image may be a film image, if the detector is film, or a digital image, if the detector is a digital detector. The projected pattern of the radiopaque markers 320 is used to determine the orientation of at least one reference material 310 in space with respect to the defined origin. This is accomplished by using a transformation matrix (translation, rotation or both) to transform the coordinates of the radiopaque markers, create virtual projections of the radiopaque markers based on this transformation, and minimize an error function between the actual projected pattern and virtual projections made with reference material(s) 310 in different orientations of height and rotation. The new coordinates are then used to define the 3-dimensional orientation in space of reference material(s) 310. This process then allows both the height of the retaining device and the plane of the retaining device to be determined.

The following example is given for the use of a step phantom in mammography. The step phantom is adhered to the top of the compression paddle such that it projects into the unused corner of the mammogram. Thus the height and orientation of the step phantom's base is the height and orientation (tilt) of the compression paddle. By describing the step phantom's position and orientation, and the extended shape (planar or curved) of the paddle, the thickness of the breast at all image locations is described. The step phantom design preferably has at least 3 lead spheres (i.e. lead "shot") attached to the base, middle, and top. A static world 3-d coordinate system is defined with the mammography detector as the xy plane (x, y, $0)_W$, and the world origin $(0,0,0)_w$ at the point where a line drawn between the detector and the focal spot "normally" intersects the detector plane (typically in the middle of the edge where the chest wall is imaged). The focal spot in most systems is 60 cm away from the detector at $(0,0, 60)_W$. A local phantom coordinate system is defined with its origin $(0,0,0)_P$ at the base of the phantom below its side edge. To mathematically describe the position of the phantom anywhere in world coordinates space, one only has to know the position $(x, y, z)_W$ of the phantom origin and the orientation of the phantom in terms of rotation angles between the world axes and local axes ($\alpha$, $\beta$, $\theta$). This can be thought of as a translation and rotation matrix that moves the phantom's local origin from the world origin to the desired position and orientation using matrix mathematics well developed and common in the robotic industry as well as the gaming visualization field. Using the known location of the focal spot and detector in world space, and the individual locations of the lead spheres in phantom space, pseudo mammogram images can be made of the lead sphere projections for specific positions of the phantom. By minimizing the least square error function made by summing the difference between a pseudo image and an actual mammogram, the phantom's position can be precisely and accurately located with respect to the detector. Then, it is a simple matter to geometrically determine the compression thickness at the phantom (z-coordinate less the top paddle and Bucky grid thickness), and the paddle tilt (same as the phantom orientation). If it is assumed that the compression paddle is a plane, the breast area that is in contact with the paddle is explicitly known.

Using the determined position of reference material 310 and the known geometry of the imaging apparatus, regions of interest 350 can then be mapped onto at least one reference material 310 (FIG. 3C) corresponding to the different thicknesses of at least one reference material 310. In addition, the thickness of body part 330 can be determined. A graph of thickness versus attenuation values of each reference material can then be constructed, as shown in FIG. 3D. This allows creation of a calibration function of attenuation values versus thickness. Thus, the attenuation values of each reference material at the determined body part thickness can be determined. These values, in turn, can be compared to the attenuation values of body part 330 to determine the proportion of body materials defining body part 330.

In a preferred embodiment, the attenuation values of body part 330 and at least one reference material 310 are represented as pixel values. This may be done directly, in the case of a digital detector, or may be accomplished by scanning an X-ray film and converting it to a digital image. The thickness of body part 330 is then preferably determined at each pixel.

Thus, even if the thickness of body part 330 varies over the image due to non-planarity of retaining device 340, the correct proportion of body materials can be determined for each pixel.

The following example is for mammography. To find the density reference attenuations as a function of thickness using the step phantom, the mammogram is acquired with the phantom in the image and the phantom's position and orientation in world coordinates determined by the lead markers. The mammography version of the phantom has steps ranging from 1 cm to 9 cm providing not only a range of reference attenuations for each mammogram but a wide breast thickness range as well. The step attenuation values are quantified by applying the translation and rotation matrix, determined by the lead markers, to a region of interest template containing 9 squares, $ROI_1$ to $ROI_9$, located at the height and position of each step, and one larger base square region, $ROI_0$. This translated and rotated template is projected onto the mammogram showing the position of the top of each step as well as the base. Valid attenuations are found in the areas in non-union with the other ROIs but in union with the base. The actual Boolean expression for ROI1 is: $ROI_{1\_valid} = (ROI_1 \cap ROI_0) \cap \overline{(ROI_2 \cap ROI_3 \cap ROI_4 \cap ROI_5 \cap ROI_6 \cap ROI_7 \cap ROI_8 \cap ROI_9)}$ A similar expression is used for each of the other ROIs. Union (overlap) of the ROIs is caused by parallax in the x-ray projections and exasperated by paddle tilt and is different for different breast heights. A bias angle can be used in the step phantom to minimize parallax overlap of the ROIs at an average breast thickness (i.e. 4 cm). The edges of the step phantom can also be flared to broaden the base and increase the valid ROI size (union of the base ROI and the steps). The valid ROI attenuations for lean and fat are plotted as a function of thickness. The lean attenuations are acquired directly from the phantom, if the phantom has an attenuation characteristic of a glandular tissue. If only one material is used in the step phantom (i.e. lean or glandular), the other reference values (i.e. fat) are derived from the kVp settings and measured reference values (i.e. lean). Finally, the breast pixel attenuation is compared to the fat and lean reference curve for the breast's thickness and a specific fat and lean volume determined to create that attenuation. The whole breast $BD_{SXA}$ value is the sum of all the pixel fat volumes divided by the total volume times 100.

The proportion of body materials at each pixel may be used to calculate, for example, the absolute mass density of the body part at each pixel. For example, in the breast using the method according to the present invention, the fat mass and the lean mass is found for each pixel as well as the volume of fat and volume of lean since they are related by the known and constant material density ($g/cm^3$) of each. The mass density is found by summing the fat mass over the entire breast and dividing by the total mass (fat+lean mass). A threshold may then be set and pixels identified that have an absolute mass density value above the threshold value. For example, the threshold could be set to 30% mass density (where mass density equals high density mass/(high density mass+low density mass) for a given pixel). This allows for all pixels above 30% mass density (i.e. the high density pixels) to be automatically identified after the pixels are calibrated in units of mass density. The ratio of the number of high density pixels (or area) to the total number of pixels (or area) can then be calculated. This ratio may be of clinical significance. For example, this ratio is equal to a previously defined breast cancer risk factor called mammographic density. This method of automatically identifying pixels having a mass density above a defined threshold could be used with any method that allows the absolute mass density of a body part at each pixel to be calculated. Examples include U.S. Pat. Nos. 6,516,045 and 6,654,445, both by Shepherd et al., which are incorporated by reference herein.

In one embodiment, the method includes a number of additional steps. One step includes collecting data relating to the above-described irradiating, positioning, detecting, body part thickness determination, and attenuation value determination. These data may include, for example, X-ray technique, kVp, mAs, body part thickness, body part projected area, body part compression force, body part projected geometry, retaining device angle, reference material attenuation values, film linearity to X-ray dose, and radiographic uniformity of the detected beams. The validity of the attenuation values for the at least one reference material is then determined. Validity checks may include, but are not limited to, determining whether the attenuation values are in the usable range of the detector and calculating a ratio of attenuation values from the at least one reference material. Once the attenuation values have been validated, the collected data may be used to create a regression model. This model may then be used to predict attenuation values for reference materials. Preferably, the regression model is then tested by comparing the predicted attenuation values to actual attenuation values for the at least one reference material. For example, many mammograms may be acquired with a step phantom such that true breast density is known. Then, the model would be trained on a portion of these mammograms such that covariants that predict the attenuation in the reference materials are described via a multivariant regression model. The remaining mammograms not used for training would be used to test the model by comparing the derived density from no phantom to the breast density measured with the phantom.

In another embodiment, the regression model is created using the following method. First, a device is provided for retaining the body part. Next, at least two reference materials are provided, where each of the reference materials has attenuation characteristics that are selected in correspondence to the body materials. The at least two reference materials are positioned adjacent to the retaining device. Next, the body part and the at least two reference materials are simultaneously irradiated, thereby creating beams that are attenuated by the body part and the reference materials. These attenuated beams are detected as attenuation values by a detector. Data are then collected relating to the irradiating, positioning and detecting and the validity of the attenuation values is determined as described above. In this embodiment, no radiopaque markers are used and the reference materials need not have multiple thicknesses.

The present invention also provides a method of determining a proportion of body materials in a body part using either of the above-described regression models. In a first step, a device is provided for retaining the body part. Next, the body part is irradiated, thereby creating beams that are attenuated by the body part. These attenuated beams are then detected as attenuation values by a detector. Finally, the proportion of body materials defining the body part is calculated by comparing the attenuation values of the body part to the attenuation values predicted by the regression model, as described above for a physical phantom.

Preferably, the attenuation values of the body part are represented as pixel values. In this case, an absolute mass density can be calculated for each pixel, a threshold value can be set, pixels may be identified that have absolute mass densities above the threshold value, and a ratio of pixels with an absolute mass density above the threshold value and the total number of pixels can be calculated, as described above.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of determining a proportion of body materials in a body part, comprising the steps of:
    a) providing a device for retaining said body part;
    b) providing at least one reference material with at least two thicknesses, wherein each of said at least one reference material has an attenuation characteristic, and wherein said attenuation characteristic is selected in correspondence to said body materials;
    c) positioning said at least one reference material adjacent to said device;
    d) positioning at least three radiopaque markers on said at least one reference material;
    e) simultaneously irradiating said body part, said at least one reference material and said radiopaque markers, thereby creating beams that are attenuated by said at least one material and said body part and thereby projecting a pattern from said radiopaque markers;
    f) detecting said beams that are attenuated by said at least one reference material and said body part as attenuation values with a detector;
    g) determining the thickness of said body part from said pattern;
    h) determining said attenuation values for said at least one reference material at said determined thickness; and
    i) calculating said proportion of said body materials defining said body part by comparing said attenuation values of said body part to said determined attenuation values for said at least one reference material at said determined thickness.

2. The method as set forth in claim 1, wherein said body part is selected from the group consisting of breast, organ, bone, muscle and processed tissue and said proportion is selected from the group consisting of breast density, organ density, bone density, muscle density and processed tissue density.

3. The method as set forth in claim 1, wherein said attenuation characteristic of said at least one reference material is equivalent to an attenuation characteristic of a fat tissue.

4. The method as set forth in claim 1, wherein said attenuation characteristic of said at least one reference material is equivalent to an attenuation characteristic of a glandular tissue.

5. The method as set forth in claim 1, wherein said device comprises a top radiolucent paddle, with a top surface and a bottom surface, and a bottom radiolucent paddle, with a top surface and a bottom surface.

6. The method as set forth in claim 5, wherein said body part is retained between said bottom surface of said top radiolucent paddle and said top surface of said bottom radiolucent paddle.

7. The method as set forth in claim 5, wherein said at least one reference material is positioned on said top surface of said top radiolucent paddle.

8. The method as set forth in claim 1, further comprising attaching said at least one reference material to said device.

9. The method as set forth in claim 1, wherein said step of providing a retaining device further comprises the step of providing a device for adjusting said retaining device to retain body parts of different thicknesses.

10. The method as set forth in claim 1, comprising providing at least five radiopaque markers.

11. The method as set forth in claim 1, wherein said radiopaque markers comprise metallic spheres.

12. The method as set forth in claim 1, further comprising representing said attenuation values as pixel values.

13. The method as set forth in claim 12, wherein said thickness of said body part is determined at each pixel.

14. The method as set forth in claim 12, further comprising
    a) calculating the absolute mass density for each of said pixels;
    b) setting a threshold value for said absolute mass density of said pixels;
    c) identifying pixels with an absolute mass density above said threshold value; and
    d) calculating the ratio of said pixels with an absolute mass density above said threshold value and total number of pixels.

15. The method as set forth in claim 1, wherein at least two reference materials are provided.

16. The method as set forth in claim 15, wherein said attenuation characteristic of one of said reference materials is equivalent to an attenuation characteristic of a fat tissue, and said attenuation characteristic of another of said reference materials is equivalent to an attenuation characteristic of a glandular tissue.

17. The method as set forth in claim 1, further comprising:
    a) collecting data relating to said irradiating, said positioning, said detecting, said determining of said thickness, and said determining of said attenuation values;
    b) determining the validity of said attenuation values for said at least one reference material;
    c) creating a regression model of said collected data; and
    d) utilizing said regression model to predict attenuation values for said at least one reference material.

18. The method as set forth in claim 17, wherein said data are selected from the group consisting of X-ray technique, kVp, mAs, body part thickness, body part projected area, body part compression force, body part projected geometry, retaining device angle, reference material attenuation values, film linearity to X-ray dose, and radiographic uniformity of said detected beams.

19. The method as set forth in claim 17, wherein said determining of said validity comprises determining whether said attenuation values are in the usable range of said detector.

20. The method as set forth in claim 17, wherein said determining of said validity comprises calculating a ratio of said attenuation values from said at least one reference material.

21. The method as set forth in claim 17, further comprising testing said regression model by comparing said predicted attenuation values to actual attenuation values of said at least one reference material.

22. A method of determining a proportion of body materials in a body part using the regression model as set forth in claim 17, comprising the steps of:
    a) providing a device for retaining said body part;
    b) irradiating said body part, thereby creating beams that are attenuated by said body part;
    c) detecting said beams that are attenuated by said body part as attenuation values;
    d) calculating said proportion of said body materials defining said body part by comparing said attenuation values of said body part to said attenuation values predicted by said regression model.

23. The method as set forth in claim 22, further comprising representing said attenuation values as pixel values.

24. The method as set forth in claim 23, further comprising:
   a) calculating the absolute mass density for each of said pixels;
   b) setting a threshold value for said absolute mass density of said pixels;
   c) identifying pixels with an absolute mass density above said threshold value; and
   d) calculating the ratio of said pixels with an absolute mass density above said threshold value and total number of pixels.

25. The method as set forth in claim 1, wherein said at least one reference material and said at least three radiopaque markers are positioned such that said beams that are attenuated by said at least one material and said projected pattern of said radiopaque markers do not interfere with said beams that are attenuated by said body part.

26. A method of creating a regression model for determining a proportion of body materials in a body part, comprising the steps of:
   a) providing a device for retaining said body part;
   b) providing at least two reference materials, wherein each of said at least two reference materials have attenuation characteristics, and wherein said attenuation characteristics are selected in correspondence to said body materials;
   c) positioning said at least two reference materials adjacent to said device;
   d) simultaneously irradiating said body part and said at least two reference materials, thereby creating beams that are attenuated by said at least two materials and said body part;
   e) detecting said beams that are attenuated by said at least two reference materials and said body part as attenuation values with a detector;
   f) collecting data relating to said irradiating, said positioning and said detecting;
   g) determining the validity of said attenuation values for said at least two reference materials;
   h) creating a regression model of said collected data; and
   i) utilizing said regression model to predict attenuation values for said at least two reference materials.

27. The method as set forth in claim 26, wherein said data are selected from the group consisting of X-ray technique, kVp, mAs, body part thickness, body part projected area, body part compression force, body part projected geometry, retaining device angle, reference material attenuation values, film linearity to X-ray dose, and radiographic uniformity of said detected beams.

28. The method as set forth in claim 26, wherein said determining of said validity comprises determining whether said attenuation values are in the usable range of said detector.

29. The method as set forth in claim 26, wherein said determining of said validity comprises calculating a ratio of said attenuation values from said at least two reference materials.

30. The method as set forth in claim 26, further comprising testing said regression model by comparing said predicted attenuation values to actual attenuation values of said at least two reference materials.

31. A method of determining a proportion of body materials in a body part using the regression model as set forth in claim 26, comprising the steps of:
   a) providing a device for retaining said body part;
   b) irradiating said body part, thereby creating beams that are attenuated by said body part;
   c) detecting said beams that are attenuated by said body part as attenuation values;
   d) calculating said proportion of said body materials defining said body part by comparing said attenuation values of said body part to said attenuation values predicted by said regression model.

32. The method as set forth in claim 31, further comprising representing said attenuation values as pixel values.

33. The method as set forth in claim 32, further comprising:
   a) calculating the absolute mass density for each of said pixels;
   b) setting a threshold value for said absolute mass density of said pixels;
   c) identifying pixels with an absolute mass density above said threshold value; and
   d) calculating the ratio of said pixels with an absolute mass density above said threshold value and total number of pixels.

34. An apparatus for determining a proportion of body materials in a body part, comprising:
   a) a device for retaining said body part;
   b) at least one reference material with at least two thicknesses positioned adjacent to said retaining device, wherein each of said at least one reference material has an attenuation characteristic, and wherein said attenuation characteristic is selected in correspondence to said body materials;
   c) at least three radiopaque markers positioned on said at least one reference material;
   d) a radiation device positioned to simultaneously irradiate said body part, said at least one reference material and said radiopaque markers;
   e) a detector to detect beams attenuated through said body part and said at least one reference material as attenuation values, and to detect a pattern projected from said irradiated radiopaque markers; and
   f) a calculation device for determining the thickness of said body part from said pattern and for calculating said proportion of said body materials defining said body part based on comparing said attenuation values of said body part to said attenuation values of said at least one reference material at said determined thickness.

35. The apparatus as set forth in claim 34, wherein said body part is selected from the group consisting of breast, organ, bone, muscle and processed tissue and said proportion is selected from the group consisting of breast density, organ density, bone density, muscle density and processed tissue density.

36. The apparatus as set forth in claim 34, wherein said attenuation characteristic of said at least one reference material is equivalent to an attenuation characteristic of a fat tissue.

37. The apparatus as set forth in claim 34, wherein said attenuation characteristic of said at least one reference material is equivalent to an attenuation characteristic of a glandular tissue.

38. The apparatus as set forth in claim 34, wherein said at least one reference material and said at least three radiopaque markers are positioned such that said beams that are attenuated by said at least one material and said projected pattern of said radiopaque markers do not interfere with said beams that are attenuated by said body part.

39. The apparatus as set forth in claim 34, comprising at least two reference materials.

40. The apparatus as set forth in claim 39, wherein said attenuation characteristic of one of said reference materials is equivalent to an attenuation characteristic of fat tissue, and said attenuation characteristic of another of said reference materials is equivalent to an attenuation characteristic of a glandular tissue.

41. The apparatus as set forth in claim 34, wherein said retaining device comprises a top radiolucent paddle, with a top surface and a bottom surface, and a bottom radiolucent paddle, with a top surface and a bottom surface.

42. The apparatus as set forth in claim 41, wherein said retaining device is designed to retain said body part between said bottom surface of said top radiolucent paddle and said top surface of said bottom radiolucent paddle.

43. The apparatus as set forth in claim 41, wherein said at least one reference material is positioned on said top surface of said top radiolucent paddle.

44. The apparatus as set forth in claim 34, wherein said at least one reference material is attached to said retaining device.

45. The apparatus as set forth in claim 34, wherein said retaining device further comprises a device for adjusting said retaining device to retain body parts of different thicknesses.

46. The apparatus as set forth in claim 34, comprising at least five radiopaque markers.

47. The apparatus as set forth in claim 34, wherein said radiopaque markers comprise metallic spheres.

48. The apparatus as set forth in claim 34, wherein said radiation device is a single energy X-ray absorptiometer, a single photon absorptiometer, a mammography system, or a planar medical X-ray system.

* * * * *